(12) United States Patent
Gormley et al.

(10) Patent No.: US 8,053,513 B2
(45) Date of Patent: Nov. 8, 2011

(54) PYRROLIDONE-CARBOXYLIC MODIFIED POLYSILOXANES HAVING AQUEOUS AND DETERGENT SOLUBILITIES AND WATER-IN-OIL EMULSION CAPABILITY

(75) Inventors: John L Gormley, Midland Park, NJ (US); Ramannair S Premachandran, Saddle Brook, NJ (US); Steven J Anderson, Hartlepool (GB)

(73) Assignee: Uniqema Americas LLC, Wilmington, DE (US)

( * ) Notice: Subject to any disclaimer, the term of this patent is extended or adjusted under 35 U.S.C. 154(b) by 761 days.

(21) Appl. No.: 11/587,774

(22) PCT Filed: Apr. 28, 2005

(86) PCT No.: PCT/US2005/014442
§ 371 (c)(1),
(2), (4) Date: Sep. 4, 2007

(87) PCT Pub. No.: WO2005/111115
PCT Pub. Date: Nov. 24, 2005

(65) Prior Publication Data
US 2008/0138301 A1    Jun. 12, 2008

Related U.S. Application Data

(60) Provisional application No. 60/567,064, filed on Apr. 30, 2004.

(51) Int. Cl.
*C08L 83/00* (2006.01)
(52) U.S. Cl. .......................... 524/588; 524/156; 528/27
(58) Field of Classification Search .................... 528/27; 524/156, 588
See application file for complete search history.

(56) References Cited

U.S. PATENT DOCUMENTS
6,565,837 B2 * 5/2003 Fost et al. .................. 424/70.12

OTHER PUBLICATIONS
International Search Report dated Jul. 13, 2005 for PCT/US2005/014442.

* cited by examiner

*Primary Examiner* — Edward Cain
(74) *Attorney, Agent, or Firm* — Jones Day

(57) ABSTRACT

The properties of 2-pyrrolidone-4-carboxylic substituted polysiloxanes can be dramatically altered by increasing the presence of the carboxylic-substituted pyrrolidone monomer of the polysiloxane, such that the amidopolysiloxane has an acid equivalent weight of about 3:00-3,000 daltons and a molecular weight average Mw of about 1,000-60,000 daltons resulting in enhanced detergent and water solubilities and the ability to form water-in-oil emulsions thereby providing usefulness across a broad range of formulations having enhanced electrolytic and silicone and/or hydrocarbon compatibility and cleansing properties.

27 Claims, No Drawings

PYRROLIDONE-CARBOXYLIC MODIFIED POLYSILOXANES HAVING AQUEOUS AND DETERGENT SOLUBILITIES AND WATER-IN-OIL EMULSION CAPABILITY

CROSS REFERENCE TO RELATED APPLICATIONS

This application is the National Phase application of International Application No. PCT/US2005/014442, filed Apr. 28, 2005, which designates the United States and was published in English, and which further claims priority from U.S. Provisional Application No. 60/567,064, filed Apr. 30, 2004. These applications, in their entirety, are incorporated herein by reference.

The present invention recognizes the properties of 2-pyrrolidone-4-carboxylic substituted polysiloxanes can be dramatically altered by increasing the presence of the carboxylic-substituted pyrrolidone monomer portion of the polysiloxane, such that the resultant amidopolysiloxane has an acid equivalent weight of about 300-3,000 daltons and a molecular weight $M_w$ of about 1,000-60,000 daltons resulting in enhanced detergent and water solubilities and the ability to form water-in-oil emulsions.

Organosilicone fluids, including polydimethylsiloxanes, have a wide variety of properties including lubricity, water repellency, permeability to gases, dielectric properties, low surface tension and resistance to high temperatures, weathering and oxidation. Consequently, silicone fluids are found in a wide number of commercial products including lubricants, coolants, protective coatings, water repellents, surfactants, wetting agents, anti-foaming agents for liquids, brake fluids, personal care and other cosmetic products, adhesives, dielectric fluids, textile finishes, polishes, mold release agents, sealants and rust preventatives.

Although silicone fluids tend to be soluble in a wide variety of polar organic oils and solvents, they are not water-miscible or -soluble nor fully detergent soluble resulting in transparent formulations. However, there are numerous means for modifying the silicone backbone (copolymerization) to enhance its hydrophilicity and/or lipophilic properties. Examples include modifying the silicone backbone to modify its interactions between the oil and water phases with the addition of: ($C_2$-$C_3$)alkoxyalkylene moieties, e.g., —$(CH_2)_n$-$EO_m$—$PO_p$—OH; ($C_2$-$C_3$)alkoxylenealiphatic hydrocarbon moieties, e.g., —$(CH_2)_n$-$EO_n$—$PO_p$—$(CH_2)_x$—$CH_3$; or an aliphatic hydrocarbon, e.g., —$(CH_2)_x$—$CH_3$; where n, m, p and x refer to the number of indicated substituents and are preferably integers up to about 50. The ethylene oxide moieties tend to increase hydrophilicity, the propylene oxide moieties tend to increase or balance the hydrophobicity and aliphatic hydrocarbons tend to increase hydrophobicity and can also be used to solidify the siloxane. However, the copolymerization of the silicone with ethyleneoxy and propyleneoxy moieties essentially dilutes the silicone effect provided by the siloxane polymer backbone.

Organosilicones having carboxyl substituted pyrrolidone group or an amidoamine derivative thereof are disclosed as part of a broad group of organosilicones in U.S. Pat. No. 5,596,061. However, these compositions do not directly exhibit water compatibility or detergent solubility (col. 1, lines 31-42). To obtain water solubility requires a further reaction to prepare, for example, a silicone-containing phospholipid (col. 1, lines 38-42). However, Monasil PLN phospholipid silicone, commercially available from Uniqema, New Castle, Del., USA, is a twenty-five weight percent concentrate in water which is a translucent two-phase dispersion.

For the purposes of this invention, molecular weight $M_n$ is the mean number average polymer weight measured by gel permeation chromatography (GPC). Molecular weight $M_w$ is the mean polymer weight average of the polymer as estimated by correlation to polydimethylsiloxane fluid viscosity, an industry accepted technique. Total Acid Number is the number of milligrams of potassium hydroxide (KOH) required to neutralize the acid groups in a gram of the polymer. Acid Equivalent Weight is the mass of polymer containing one mole of acid groups expressed as grams/mole and is that amount which would combine with one mole of potassium hydroxide. Detergent includes surfactants, surface active agents and combinations thereof. Dispersion, or detergent dispersible, refers to a two phase system where the polysiloxane is in a separate phase from the water phase and the dispersion is not clear. Detergent solubility refers to a composition where inclusion of the carboxy pyrrolidone amidopolysiloxanes of this invention forms a clear system in the presence of water and a detergent. Descriptions of detergents (surfactants and surface agents) are provided infra. Water solubility refers to a composition where the carboxy pyrrolidone amidopolysiloxanes of this invention are sufficiently ionized to form a clear system in an aqueous system, without the presence of detergent.

The 2-pyrrolidone-4-carboxylic substituted polysiloxanes composition of the present invention, also referred to as amidopolysiloxanes, is represented by a random polymer of Formula 1 comprising:

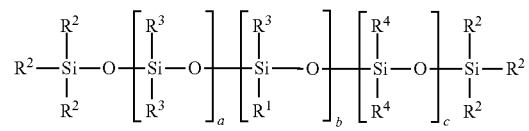

wherein: $R^1$ is a pyrrolidone-containing functional group as shown in Formula 2:

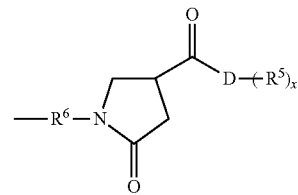

D is oxygen or nitrogen, wherein at least 50% on a molar basis of D is oxygen;

$R^5$ is hydrogen, ($C_1$-$C_{22}$)alkyl or polyoxy($C_2$-$C_3$)alkylene of 2 to 200 units, wherein at least 50% on a molar basis of $R^5$ is hydrogen.

x is 1 or 2;

$R^6$ is branched or unbranched ($C_{1-20}$)alkyl;

each $R^2$, which can be independently the same or different, is selected from ($C_1$-$C_4$)alkyl, phenyl or —$OR^7$ wherein $R^7$ is hydrogen or lower ($C_{1-6}$)alkyl, wherein collectively $R^2$ is substantially capped moieties;

each $R^3$, which can be independently the same or different, is selected from ($C_1$-$C_4$)alkyl or phenyl;

each $R^4$, which can be independently the same or different, is selected from phenyl, ($C_{1-36}$)alkyl, ($C_{1-36}$)alkenyl, and/or ($C_{1-20}$)alkyl-capped or uncapped polyoxy($C_2$-$C_3$)alkylene of 2 to 200 units;

a is an integer from 10 to 560;

b is an integer from 1 to 40, wherein the absolute ratio of a to b is about 2.5 to about 35 and wherein the average integer sum of a+b exists in the range of 11 to 600 and preferably about 50 to about 400 and more preferably from about 150 to about 350;

c is an integer from 0 to 10, wherein the absolute ratio of b to c is no less than about 4.

As known by those familiar with silicone chemistry, the distribution of a, b and c polymer subunits of Formula 1 are randomly arranged, hence termed a random polymer. The carboxy pyrrolidone structure of Formula 1 is primarily obtained from the reaction of a pendant primary amine source and itaconic acid or ester. As such, a portion of $R^1$ can be a primary amine (—$R^6$—$NH_2$), essentially an unreacted by-product that may or may not be desired in the final product.

The term capped in reference to $R^2$ is where a silicone-carbon bond exists which is not readily hydrolyzed. Similarly, the term uncapped refers to $R^2$ when it is —$OR^7$, since it can be reacted or hydrolyzed or can bond to substrates or increase the polymer molecular weight by condensation. $R^2$ is preferably substantially alkyl-capped. The terms uncapped or alkyl capped in reference to the polyoxyalkylenes of $R^4$ refers to the polyoxyalkylene chain ending in —OH (uncapped) or continues with an ether linkage (capped).

Another aspect of Formula 1 comprises amidopolysiloxanes where:

$R^1$, the pyrrolidone-containing functional group,

D is oxygen;

$R^5$ is hydrogen, ($C_1$-$C_6$)alkyl or a polyoxy ($C_2$-$C_3$)alkylene of 1 to 6 units, wherein at least 50% on a molar basis of $R^5$ is hydrogen.

$R^6$ is a branched or unbranched ($C_3$-$C_4$)alkyl;

each $R^2$ is selected from methyl, phenyl, —$OR^7$ where $R^7$ is methyl, ethyl or hydrogen and collectively $R^2$ is substantially capped moieties;

each $R^3$ is selected from methyl or phenyl;

each $R^4$ is selected from phenyl, methyl, ($C_{1-36}$)alkyl, or ($C_{1-20}$)alkyl-capped or uncapped polyoxy($C_2$-$C_3$)alkylene of 1 to 30 units;

a is an integer from 10 to 560;

b is an integer from 1 to 40, wherein the absolute ratio of a to b is about 2.5 to about 35, with a preferred ratio of 20-26;

and the average integer sum of a+b exists in the range 11 to 600 and preferably about 11 to about 400, and more preferably from about 150 to about 350; and c is an integer from 0 to 10, wherein the absolute ratio of b to c is no less than about 4.

Another aspect of Formula 1 comprises amidopolysiloxanes where:

$R^2$ is methyl; $R^3$ is methyl; $R^5$ is hydrogen; D is oxygen; $R^6$ is propyl or isobutyl;

a is an integer from 10 to 560; b is an integer from 1 to 40, wherein the absolute ratio of a to b is about 2.5 to about 35, and the average integer sum of a+b exists in the range of about 11 to about 400, more preferably from about 150 to about 350; and c is 0.

The amidopolysiloxane compositions of the present invention will have a molecular weight average $M_w$ of about 1,000-60,000 daltons and an acid equivalent weight of about 300-3,000 daltons. By varying these parameters within these ranges, a variety of properties related to detergent solubility, water solubility, and the ability to form water-in-oil emulsions can be affected. At times, neutralization of a portion or all of the carboxyl groups of the 2-pyrrolidone containing polysiloxane will be necessary to obtain some of these properties. These properties, in turn, provide for a variety of physical forms of the amidopolysiloxanes of Formula 1 conducive to various uses, for example, cleaning, lubrication, personal care products such as shampoos, conditioners, lotions, creams, soaps, body washes and antiperspirants.

These 2-pyrrolidone-carboxylic modified polysiloxanes have the capability to (a) be compatible in hydrocarbon and silicon oils; (b) act as emulsifiers and enable an aqueous solution to be readily dispersed in an oil phase containing silicone or hydrocarbon oils or mixtures thereof as a water-in-oil emulsion: (c) readily compatible in detergents and aqueous solutions and (d) place the 2-pyrrolidone containing polysiloxane into a physical form that allow for its incorporation into a variety of vehicles providing desirable characteristics to cleansers, hair conditioners, shampoos, lotions, creams, antiperspirants, other skin and scalp care products and cosmetics, lubricants, polishes and sealants.

The carboxyl functional amidopolysiloxanes and their corresponding ester and amide derivatives of the present invention can be prepared by techniques known in the art. See, for example, U.S. Pat. No. 6,228,967. For example, a corresponding aminopolysilicone compositions or fluids of the Formula 1, but where $R^1$ is —$R^6NH_2$, is reacted with up to about one equivalent, preferably about stoichiometric quantities, of itaconic acid or its ester per functional primary amine group(s) at an elevated temperature for the time sufficient for substantially all of the itaconic acid or its ester to react with the functional primary amine group(s). In general, from at least about 0.5, preferably from about 0.9 to about 1.1 equivalents of itaconic acid or its ester per functional primary amine group is reacted with the silicone fluid wherein substantially all the itaconic acid and preferably all the functional primary amine group(s) is reacted resulting in the formation of amidopolysiloxanes of Formula 1. The aminopolysilicone starting materials are commercially obtainable.

The reaction can be carried out neat or in an inert solvent such as a lower alkyl alcohol such as isopropanol (IPA), hydrocarbon solvent, or a silicone solvent, preferably cosmetically acceptable (described below) as desired, at elevated temperature up to about 175° C., preferably from about 90° C. to about 130° C. for about one to five hours, preferably two to three hours. The reaction readily proceeds and generally a substantially complete reaction of the itaconic acid or its ester with the available functional primary amine group(s) occurs via the Michael addition reaction of the double bond of the itaconic acid followed by immediate cyclization to form a pyrrolidone group. Routine analytical techniques for amine and acid values as well as monitoring water and/or alcohol evolution are used to determine completion of the reaction.

Itaconic acid (methylene succinic acid) or its ester derivative is a compound of the formula: $CH_2$=$C(COOR^9)CH_2COOR^9$ wherein $R^9$ which can be the same or different, is hydrogen or lower alkyl (1-6 carbon atoms). The compound itaconic acid is available commercially from Rhone Pouleuc and Pfizer Chemicals Division whereas ester derivatives thereof are available from Morflex Inc., Greensboro, N.C. The compounds are produced by known fermentation techniques although chemical synthesis methods are also known.

As the polysiloxane amine starting materials are reacted with itaconic acid to form the compositions of the present invention, the viscosity of the desired product is usually several times greater. At times, this results in compositions that are much too viscous (about 1,000,000 cPs (centipoises) or greater measured by Brookfield LVT viscometer using a spindle 4) to easily handle or to readily disperse or solubilize. Consequently, in those instances where the viscosity of the final product is too great, it is desired that the polysiloxane amine starting material be dissolved in a solvent and the reaction with the itaconic acid be carried out in the presence of the solvent at a temperature of from about 90° C. to 125° C., preferably 100° C. to 115° C. to preferably obtain substantially complete reaction of the amine groups, generally a period of about one to five hours, preferably two to three hours. It is preferred to choose solvents or combination of solvents, particularly polar solvents, with boiling or reflux points at or near the preferred reaction temperature of 90-110° C. The reaction rate can be enhanced by the use of a sealed reactor to complete the reaction using a low boiling point (less than about 90° C. at atmospheric pressure) at elevated pressure in relation to ambient pressure. Polar solvents, such as ($C_6$-$C_{18}$)alkyl esters of lower ($C_1$-$C_6$)alcohols in combination with lower ($C_2$ to $C_6$)alcohols, and mixtures thereof, are preferred since they facilitate a higher reaction temperature at ambient pressure, which will enhance the reaction rate and degree of reaction.

The lower ($C_1$-$C_6$)alcohols are commonly used as a solvent for itaconic acid; however, their presence in the final product is often not desired, as the alcohol's concentration increases, it is more apt to break an emulsion to which the final amidopolysiloxane is an ingredient. The ($C_6$-$C_{18}$)alkyl esters of lower ($C_1$-$C_6$)alcohols, although, not known as solvents for itaconic acid are compatible with the lower alcohol and the desired amidopolysiloxane. Thus, the mixture of the lower alcohol and the alkyl esters of lower alcohols allows a reduction in the presence of the alcohol in the final product, enhances the reaction rate and, often, the amidopolysiloxane is less viscous than when only an alcohol is used as the solvent. Generally, the ratio of the ($C_6$-$C_{18}$)alkyl esters of ($C_1$-$C_6$)alcohols to ($C_2$-$C_6$)alcohols will be from 1:1 to 10:1 by weight. When isopropyl alcohol, a common solvent for both itaconic acid and silicone fluids, is used preferred alkyl esters of alcohols include isopropyl myristate ester, isopropyl palmitate ester and isopropyl laurate ester.

Suitable solvents, oils, diluents and diluent oils for the amidopolysiloxanes of Formula 1 can be selected from a broad range of silicones, organo-modified silicones and/or hydrocarbon oils. Examples include isoparaffinic oils such as Isopar M (available from ExxonMobil); ($C_6$-$C_{18}$)alkyl esters of ($C_1$-$C_6$)alcohols, for example, isopropyl myristate, isopropyl palmitate and isopropyl laurate; dimethicones having cyclomethicones and cycloalkyldimethicones such as cyclotetradimethicone, cyclopentadimethicone cylcohexadimethicone and cycloheptadimethicone, wherein the dimethicone, cyclo methicones and cycloalkylmethicones have kinematic viscosity of less than about 20 centistokes; liquid triglycerides such as corn oil, canola oil; emollients, for example, squalenes; ($C_3$-$C_{12}$)alkyl alcohols including propanol, and isopropanol, and other cosmetically acceptable oils, wherein the 2-pyrrolidone-carboxylic containing polysiloxane preferably has a solubility of at least 50 grams (g) per 100 grams of solvent at room temperature. This reaction mixture can be further post-blended with compatible oils, if required. When using the oil as a solvent for the preparation of the amidopolysiloxanes of Formula 1, the temperature should generally not exceed the temperature at which the oil undergoes chemical and physical degradation which is preferably not greater than about 120° C. (at atmospheric pressure).

Of the solvents, oils and diluents useful for a particular amidopolysiloxane of the present invention, the ones yielding the lowest viscosity and of the most common use for the particular desired end use application are preferred.

The variations in properties of the 2-pyrrolidone containing polysiloxanes occur over a continuum of the ranges where a is an integer from 10 to 560; b is an integer from 1 to 40, the absolute ratio of a to b is about 2.5 to about 35 and the average integer sum of a+b exists in the range of 11 to 600. When it is desired for the amidopolysiloxane to have water-soluble properties or to be used in a cleansing formulation (detergent soluble), then the amidopolysiloxane requires at least partial neutralization of the carboxylic groups with a suitable base.

Generally, the amidopolysiloxanes of Formula 1 which are detergent soluble will have an absolute a to b ratio of about 2.5-35 with from 1-100 percent on a molar basis of the carboxyl groups are neutralized rendering the polymer composition detergent soluble. The clarity of the amidopolysiloxane of the present invention is affected by the amount of reaction by-products in the random polymer. In the instance of pure random polymer composition of Formula 1, the detergent solubility is expected to be up to about 50 percent (weight/weight) for a suitably chosen detergent.

The detergent soluble property will be more evident when the following composition is prepared comprising:
i) 90-99.9% by weight of a detergent system where such a system can be selected from a wide range of anionic, cationic, non-ionic, amphoteric surfactants that singularly or in combination form a single clear phase in water. Descriptions of detergents are provided infra. The surfactant(s) are about 5% to 50% by weight of the system;
ii) about 0.1 to 10 weight percent of the amidopolysiloxane of Formula 1, preferably 0.5 to 5 weight percent wherein a is an integer from 10 to 560; b is an integer from 1 to 40, the absolute ratio of a to b is about 2.5 to about 35, preferably about 13-33, more preferably about 20-26; and
iii) an organic or inorganic base, as described in more detail below, sufficient to neutralize 1% to 100%, preferably greater than 50%, on a molar basis of the carboxyl groups of the amidopolysiloxane. The amount of neutralization depends on the alkalinity or pH of the detergent system prior to amidopolysiloxane addition and the absolute ratio of a to b of the carboxylic containing polymer, which relates to the polarity of the polymer. The solution pH will be about 3.5-11; and preferably about 4.5-8.

Examples of specific uses are: cleansers including shampoos, body washes, soaps, facial washes, hygiene washes, and wipes; as a spreading and wetting agents; and emulsion polymerization.

Generally, the amidopolysiloxanes of Formula 1 which are water soluble will have an absolute a to b ratio of about 2.5-13 with from 50-100 percent, preferably greater than 75 percent, on a molar basis of the carboxyl groups are neutralized rendering the polymer composition water soluble. The water solubility of the amidopolysiloxane of the present invention is affected by the amount of reaction by-products in the random polymer of Formula 1. In the instance of a pure random polymer of Formula 1, the water solubility is expected to be up to about 40-50 weight/weight percent of water.

The aqueous soluble property will be more evident when the following composition is prepared comprising:
i) 90-99.9% by weight of a clear aqueous system comprised primarily of water and other optional water soluble additives;
ii) about 0.1 to 10 weight percent of the amidopolysiloxane of Formula 1, preferably 0.5 to 5 weight percent, where specifically a is an integer from 10 to 560; b is an integer from 1 to 40, the absolute ratio of a to b is about 2.5 to about 13; and
iii) an organic or inorganic base, as described in more detail below, sufficient to neutralize 50% to 100% on a molar basis of the carboxyl groups of the amidopolysiloxane.

The amount of neutralization depends on the alkalinity or pH of the aqueous system before amidopolysiloxane polymer addition and the absolute ratio, a to b, of the carboxylic containing polymer, which relates to the polarity of the polymer.

Examples of specific uses for the aqueous soluble product are: aqueous spreading and wetting agents; paper and textile treatment; and skin and hair conditioning preparations.

Neutralization refers to forming the ionized carboxylic acid group as opposed to the protonated form of the carboxylic acid and is accomplished by addition of organic or inorganic bases and/or their salts, representing a wide spectrum of assorted monovalent, divalent and/or polyvalent species. Examples include alkali metal hydroxides and carbonates such as sodium carbonate, sodium hydroxide and potassium hydroxide, ammonium hydroxide, aluminium hydroxide, alkali earth metal hydroxides such as calcium hydroxide, magnesium hydroxide, alkanolamines such as MEA (monoethanolamine), DEA (diethanolamine) or TEA (triethylethanolamine), other amines such as silicone amines, lauryl amine and ($C_6$-$C_{22}$)aliphatic amines and product mixtures that contain excess alkalinity from one or more bases in this list. The base is added in an amount sufficient to solubilize the amidopolysiloxane into a clear formulation or an enhanced emulsification stability. Generally, complete neutralization will require a pH of about 6.5. When the formulation or composition into which the amidopolysiloxane is being added has a pH of greater than neutral to about 12, self-neutralization may occur. The ultimate pH is dependent upon the desired use of the formulation.

Generally, it was found that by neutralizing the carboxylic groups it imparted foaming and enhanced (a) water solubility or (b) detergent solubility. When the amidopolysiloxanes were not neutralized, they exhibited the expectant anti-foaming characteristics of silicones.

Neutralization can occur at any step in the process of incorporating these the amidopolysiloxanes, for example, the polymer can be dispersed in an aqueous or detergent system and then a base added to form the clarified aqueous or detergent product; or the polymer can be preneutralized prior to addition to the aqueous or detergent system; or the water phase pH adjusted appropriately prior to polymer addition.

Generally, the water-in-oil emulsion properties will be more evident when a is an integer from 10 to 560; b is an integer from 1 to 40, the absolute ratio of a to b is about 13 to about 35, preferably about 15-33, more preferably about 22-26; wherein the average integer sum of a+b exists in the range of 11 to 600 and preferably about 50 to about 400 and more preferably from about 150 to about 350. When c is zero and the amidopolysiloxane is used in a water-in oil emulsion, then the emulsion exhibits better sensory feel compared to emulsifiers known in the art containing pendant alkoxylate functionality on the polysiloxane. Neutralization of a portion or all of the carboxyl groups of the amidopolysiloxane may be desired to obtain the optimum water-in-oil emulsion characteristics. Examples of specific uses are: polishes; mold release agents; wipes; sun screens; antiperspirants; make-up removers; skin creams and lotions; hair crèmes; color cosmetics; active delivery vehicles; and hair color preparations.

The amidopolysiloxanes can be formulated into water-in-oil emulsions comprising:
(a) about 0.1 to about 5, preferably 0.25 to about 2, weight/weight percent of the amidopolysiloxane of Formula 1, wherein the carboxylic group may contain some ester and/or amide functional groups, but is preferably in the free acid form;
(b) about 8 to about 60 weight/weight percent of an oil phase comprised of either silicone, organosilicone and/or hydrocarbon containing oils (as previously described above); and
(c) about 40 to about 90 weight/weight percent of a water phase of pH about 2 to about 12, containing about 0.1 to about 40 weight percent added electrolyte.

As the amount of the amidopolysiloxane begins exceeding 2 weight percent of the emulsion, and the greater it becomes, the potentially less stable the emulsion becomes. More preferably, the water-in-oil emulsion will comprise about 0.25-1 weight/weight percent of the amidopolysiloxane and from 20-40 weight/weight percent oil.

The amount of electrolyte in the emulsion is application dependent. For example, an antiperspirant emulsion generally contains about 20-30 weight percent and a deodorant emulsion generally contains about 10-15 weight percent electrolyte. Electrolytes and their use are readily known by those in the emulsion art and include salts of Group IA and IIA alkali metals including sodium, potassium, magnesium, calcium, salts of Group IVB metals including titanium and zirconium, salts of Group IIB metals including zinc and salts of Group IIIA metals including aluminum and their combinations including those coupled with chlorohydrates.

The emulsion is prepared by blending the amidopolysiloxane with the oil phase and then adding and mixing in or homogenizing the water or aqueous phase. The water-in-oil emulsion can be blended at ambient (room) temperature by applying a minimum amount of mechanical shear energy such that re-dispersible and/or stable emulsions are prepared.

The oil (b) and/or water (c) phases can optionally contain a wide assortment of other active and inactive materials as known to those in the art of formulating emulsions. Examples include sunscreen actives, preservatives, vitamins, pigments such as titanium and zinc oxides, color and fragrance.

Other oil compatible additives may also be present or added to the diluent oils containing the amidopolysiloxane such as a co-emulsifier, preferably nonionic having an HLB (hydrophilic to lipophilic balance) of 4 to 12, including polyoxyethylene (POE) alcohols, POE sorbitan esters, polysorbate esters and PEG (polyethylene glycol) esters such as Arlatone P135 (polyhydroxystearic PEG ester available from Uniqema, Del., USA); film forming polymers, stabilizing polymers, preservatives, essential oils, fragrances, colors, drug actives, vitamins, waxes, thickeners, and UV active materials like sunscreens.

The amidopolysiloxanes can also be made into masterbatches comprising an oil phase component and the amidopolysiloxane, prior to combining with the water phase to form an emulsion. An example of one technique is the reaction of an equivalent amount of aminopolysiloxane starting materials, based on amine equivalent, with about 0.5 to about 1.10 molar equivalents of itaconic acid, preferably in the presence of an amount of compatible inert oil-phase diluent (as required when the neat reaction gets too thick to pour freely). Reaction conditions are essentially as described above, in Examples 12-14 below and in the series of patents assigned to Mona Industries (for example, U.S. Pat. No. 6,228,967 wherein reaction temperatures of about 90° C. to about 125° C. were sufficient to complete the reaction in just a few hours), thus preparing essentially all acid functionality on the $R^1$ pyrrolidone-containing functional group.

Another method for preparation of a masterbatch is blending the amidopolysiloxane with a primary diluent oil or mixed oil phase, preferably at temperatures between about 20° C. and about 90° C.; wherein oil phase can contain a broad range silicone, organo-modified silicone, and/or hydrocarbon containing fluids, as previously described; and optional oil compatible functional materials, including but not limited to, co-emulsifying low 4-12 HLB surfactants (e.g. Arlatone P135), film forming polymers, stabilizing polymers, preservatives, essential oils, fragrances, colors, drug actives, vitamins, waxes, thickeners, and UV active materials like sunscreens.

The pH and/or electrolytic strength of the water phase may be adjusted to lesser or greater degrees with organic or inorganic acids, bases and/or their salts, thus representing a wide spectrum of assorted monovalent, divalent and/or polyvalent species. Other optional water compatible functional materials may include, but are not limited to, water soluble glycols, diols, polyols, preservatives, colors, deodorants, antiperspirant salts, high HLB surfactants, sunscreen actives, vitamins, thickeners, hydrocolloids, dispersed phases (like kaolin clays) and the like. The water phase adjustments will be specifically tailored to influence final emulsion properties, including but not limited to, overall emulsion stability, internal droplet structure and size distribution, tactile feel, viscosity, and internal-phase ingredient stability and delivery kinetics.

The amidopolysilicones of the present invention may be incorporated in a wide variety of detergent systems that include one or more surfactants and surface active agents. Examples of surfactants and surface active agents include anionic, cationic, nonionic, amphoteric or zwitterionic surfactants as described in further detail below.

Anionic surfactants include alkyl and alkyl ether sulfates. These materials have the respective formulae $ROSO_3M$ and $RO(C_2H_4O)_xSO_3M$, wherein R is alkyl or alkenyl of from about 8 to about 30 carbon atoms, x is 1 to about 10, and M is hydrogen or a cation such as ammonium, alkanolammonium (e.g., triethanolammonium), a monovalent metal cation (e.g., sodium and potassium), or a polyvalent metal cation (e.g., magnesium and calcium). Desirably, M should be chosen such that the anionic surfactant component is water soluble. The anionic surfactant or surfactants should be chosen such that the Krafft temperature is about 15° C. or less, preferably about 10° C. or less, and more preferably about 0° or less.

Krafft temperature refers to the point at which solubility of an ionic surfactant becomes determined by crystal lattice energy and heat of hydration, and corresponds to a point at which solubility undergoes a sharp, discontinuous increase with increasing temperature. Each type of surfactant will have its own characteristic Krafft temperature. Krafft temperature for ionic surfactants is, in general, well known and understood in the art. A visual indicator of when the Krafft point has been reached is when the solution becomes cloudy as temperature is lowered.

In the alkyl and alkyl ether sulfates described above, desirably R has from about 12 to about 18 carbon atoms in both the alkyl and alkyl ether sulfates. The alkyl ether sulfates are typically made as condensation products of ethylene oxide and monohydric alcohols having from about 8 to about 24 carbon atoms. The alcohols can be derived from fats, e.g., coconut oil, palm oil, tallow, or the like, or the alcohols can be synthetic. Such alcohols are reacted with 1 to about 10, and especially about 3, molar proportions of ethylene oxide and the resulting mixture of molecular species having, for example, an average of 3 moles of ethylene oxide per mole of alcohol, is sulfated and neutralized.

Specific examples of alkyl ether sulfates which can be used in the present invention are sodium and ammonium salts of coconut alkyl triethylene glycol ether sulfate; tallow alkyl triethylene glycol ether sulfate, and tallow alkyl hexaoxyethylene sulfate. Preferred alkyl ether sulfates are those comprising a mixture of individual compounds, said mixture having an average alkyl chain length of from about 12 to about 16 carbon atoms and an average degree of ethoxylation of from 1 to about 4 moles of ethylene oxide. Such a mixture also comprises from 0% to about 20% by weight of $C_{12-13}$ compounds; from about 60% to about 100% by weight of $C_{14-16}$ compounds, from 0% to about 20% by weight of $C_{17-19}$ compounds; from about 3% to about 30% by weight of compounds having a degree of ethoxylation of 0; from about 45% to about 90% by weight of compounds having a degree of ethoxylation of from 1 to about 4; from about 10% to about 25% by weight of compounds having a degree of ethoxylation of from about 4 to about 8; and from about 0.1% to about 15% by weight of compounds having a degree of ethoxylation greater than about 8.

Other suitable anionic surfactants are the water-soluble salts of organic, sulfuric acid reaction products of the general formula $[R_1—SO_3-M]$ where $R_1$ is selected from the group consisting of a straight or branched chain, saturated aliphatic hydrocarbon radical having from about 8 to about 24, preferably about 10 to about 18, carbon atoms; and M is as previously described above in this section. Examples of such surfactants are the salts of an organic sulfuric acid reaction product of a hydrocarbon of the methane series, including iso-, neo-, and n-paraffins, having about 8 to about 24 carbon atoms, preferably about 12 to about 18 carbon atoms and a sulfonating agent, e.g., $SO_3$, $H_2SO_4$, obtained according to known sulfonation methods, including bleaching and hydrolysis.

Still other suitable anionic surfactants are the reaction products of fatty acids esterified with isethionic acid and neutralized with sodium hydroxide where, for example, the fatty acids are derived from coconut or palm oil; or sodium or potassium salts of fatty acid amides of methyl tauride in which the fatty acids, for example, are derived from coconut oil.

Additional suitable anionic surfactants are the succinates, examples of which include disodium N-octadecylsulfosuccinate; disodium lauryl sulfosuccinate; diammonium lauryl sulfosuccinate; tetra sodium N-(1,2-dicarboxyethyl)-N-octadecylsulfosuccinate; the diamyl ester of sodium sulfosuccinic acid; the dihexyl ester of sodium sulfosuccinic acid; and the dioctyl ester of sodium sulfosuccinic acid. Other suitable anionic surfactants are those that are derived from amino acids. Nonlimiting examples of such surfactants include N-acyl-L-glutamate, N-acyl-N-methyl-β-alanate, N-acylsarcosinate, and their salts. As well as surfactants derived from taurine, which is also known as 2-aminoethanesulfonic acid. An example of such an acid is N-acyl-N-methyl taurate.

Olefin sulfonates having about 10 to about 24 carbon atoms may also be used as a surfactant of the present invention. The term "olefin sulfonates" is used herein to mean compounds which can be produced by the sulfonation of alpha-olefins by means of uncomplexed sulfur trioxide, followed by neutralization of the acid reaction mixture in conditions such that any sulfones which have been formed in the reaction are hydrolyzed to give the corresponding hydroxy-alkanesulfonates. The sulfur trioxide can be liquid or gaseous, and is usually, but not necessarily, diluted by inert diluents, for example by liquid $SO_2$, chlorinated hydrocarbons, etc., when used in the liquid form, or by air, nitrogen, gaseous $SO_2$, etc., when used in the gaseous form. The alpha-olefins from which the olefin sulfonates are derived are mono-olefins having about 12 to about 24 carbon atoms, preferably about 14 to about 16 carbon atoms.

In addition to the true alkene sulfonates and a proportion of hydroxy-alkanesulfonates, the olefin sulfonates can contain minor amounts of other materials, such as alkene disulfonates depending upon the reaction conditions, proportion of reactants, the nature of the starting olefins and impurities in the olefin stock and side reactions during the sulfonation process.

Another class of suitable anionic surfactants is the beta-alkyloxy alkane sulfonates. These compounds have the following formula:

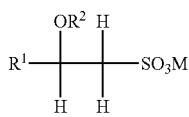

where $R^1$ is a straight chain alkyl group having from about 6 to about 20 carbon atoms, $R^2$ is a lower alkyl group having from about 1 to about 3 carbon atoms, and M is as described above. Frequently used anionic surfactants that are useful for the present invention include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, and sodium dodecyl benzene sulfonate, sodium N-lauroyl-L-glutamate, triethanol N-lauroyl-L-glutamate, sodium N-lauroyl-N-methyl taurate, sodium N-lauroyl-N-methyl-o-aminopropionate, and mixtures thereof.

Amphoteric surfactants include the derivatives of aliphatic secondary and tertiary amines in which the aliphatic radical is straight or branched and one of the aliphatic substituents contains from about 8 to about 18 carbon atoms and one contains an anionic water solubilizing group, e.g., carboxy, sulfonate, sulfate, phosphate, or phosphonate.

Zwitterionic surfactants include the derivatives of aliphatic quaternary ammonium, phosphonium, and sulfonium compounds, in which the aliphatic radicals are straight or branched, and wherein one of the aliphatic substituents contains from about 8 to about 18 carbon atoms and one contains an anionic group, e.g., carboxy, sulfonate, sulfate, phosphate, or phosphonate. A general formula for these compounds is:

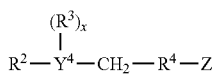

where $R^2$ contains an alkyl, alkenyl, or hydroxy alkyl radical of from about 8 to about 18 carbon atoms, from 0 to about 10 ethylene oxide moieties and from 0 to about 1 glyceryl moiety; Y is selected from the group consisting of nitrogen, phosphorus, and sulfur atoms; $R^3$ is an alkyl or monohydroxyalkyl group containing 1 to about 3 carbon atoms; X is 1 when Y is a sulfur atom, and 2 when Y is a nitrogen or phosphorus atom; $R^4$ is an alkylene or hydroxyalkylene of from 1 to about 4 carbon atoms and Z is a radical selected from the group consisting of carboxylate, sulfonate, sulfate, phosphonate, and phosphate groups.

Examples of amphoteric and zwitterionic surfactants also include sultaines and amidosultaines. Sultaines, including amidosultaines, include for example, cocodimethylpropylsultaine, stearyldimethylpropylsultaine, lauryl-bis-(2-hydroxyethyl)propylsultaine and the like; and the amidosultaines such as cocamidodimethylpropylsultaine, stearylamidododimethylpropylsultaine, laurylamidobis-(2-hydroxyethyl)propylsultaine, and the like. Preferred are amidohydroxysultaines such as the $C_{12}$-$C_{18}$ hydrocarbyl amidopropyl hydroxysultaines, especially $C_{12}$-$C_{14}$ hydrocarbyl amido propyl hydroxysultaines, e.g., laurylamidopropyl hydroxysultaine and cocamidopropyl hydroxysultaine.

Other amphoteric surfactants are the aminoalkanoates of the formula R—NH($CH_2$)$_n$COOM, the iminodialkanoates of the formula R—N[($CH_2$)$_m$COOM]$_2$ and mixtures thereof; wherein n and m are numbers from 1 to about 4, R is $C_8$-$C_{22}$ alkyl or alkenyl, and M is hydrogen, alkali metal, alkaline earth metal, ammonium or alkanolammonium.

Examples of aminoalkanoates include n-alkylamino-propionates and n-alkyliminodipropionates, specific examples of which include N-lauryl-beta-amino propionic acid or salts thereof, and N-lauryl-beta-imino-dipropionic acid or salts thereof, and mixtures thereof.

Other suitable amphoteric surfactants include those represented by the formula: where $R^1$ is $C_8$-$C_{22}$ alkyl or alkenyl, preferably $C_{12}$-$C_{16}$, $R^2$ and $R^3$ is independently selected from the group consisting of hydrogen, $CH_2CO_2M$, $CH_2CH_2OH$, $CH_2CH_2OCH_2CH_2COOM$, or $(CH_2CH_2O)_mH$

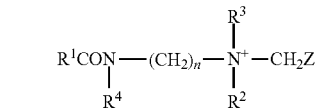

wherein m is an integer from 1 to about 25, and $R^4$ is hydrogen, $CH_2CH_2OH$, or $CH_2CH_2OCH_2 CH_2COOM$, Z is $CO_2M$ or $CH_2CO_2M$, n is 2 or 3, preferably 2, M is hydrogen or a cation, such as alkali metal (e.g., lithium, sodium, potassium), alkaline earth metal (beryllium, magnesium, calcium, strontium, barium), or ammonium. This type of surfactant is sometimes classified as an imidazoline-type amphoteric surfactant, although it should be recognized that it does not necessarily have to be derived, directly or indirectly, through an imidazoline intermediate. Suitable materials of this type are understood to comprise a complex mixture of species, and can exist in protonated and non-protonated species depending upon pH with respect to species that can have a hydrogen at $R^2$. All such variations and species are meant to be encompassed by the above formula.

Examples of surfactants of the above formula are monocarboxylates and dicarboxylates. Examples of these materials include cocoamphocarboxypropionate, cocoamphocarboxypropionic acid, cocoamphocarboxyglycinate (alternately referred to as cocoamphodiacetate), and cocoamphoacetate.

Commercial amphoteric surfactants include those sold under the trade names Miranol C2M Conc. N.P., Miranol C2M Conc. O.P., Miranol C2M Sf, Miranol CM Special (Miranol, Inc.); Alkateric 2CIB (Alkaril Chemicals); AmphoterGE W-2 (Lonza, Inc.); Monateric CDX-38, Monateric CSH-32 (Mona Industries); Rewoteric AM-2C (Rewo Chemical Group); and Schercoteric MS-2 (Scher Chemicals).

Betaine surfactants, i.e. zwitterionic surfactants, are those represented by the formula:

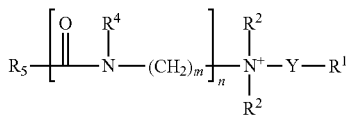

wherein: $R^1$ is a member selected from the group consisting of

COOM and CH—CH$_2$SO$_3$M $R^2$ is lower alkyl or hydroxyalkyl; $R_3$ is lower alkyl or hydroxyalkyl; $R^4$ is a member selected from the group consisting of hydrogen and lower alkyl; $R^5$ is higher alkyl or alkenyl; Y is lower alkyl, preferably methyl; m is an integer from 2 to 7, preferably from 2 to 3; n is the integer 1 or 0. M is hydrogen or a cation, as previously described, such as an alkali metal, alkaline earth metal, or ammonium. The term "lower alkyl" or "hydroxyalkyl" means straight or branch chained, saturated, aliphatic hydrocarbon radicals and substituted hydrocarbon radicals having from one to about three carbon atoms such as, for example, methyl, ethyl, propyl, isopropyl, hydroxypropyl, hydroxyethyl, and the like. The term "higher alkyl or alkenyl" means straight or branch chained saturated (i.e., "higher alkyl") and unsaturated (i.e., "higher alkenyl") aliphatic hydrocarbon radicals having from about eight to about 20 carbon atoms such as, for example, lauryl, cetyl, stearyl, oleyl, and the like. It should be understood that the term "higher alkyl or alkenyl" includes mixtures of radicals which may contain one or more intermediate linkages such as ether or polyether linkages or non-functional substituents such as hydroxyl or halogen radicals wherein the radical remains of hydrophobic character.

Examples of surfactant betaines of the above formula wherein n is zero include the alkylbetaines such as cocodimethylcarboxymethylbetaine, lauryldimethylcarboxymethylbetaine, lauryl dimethyl-alpha-carboxyethylbetaine, cetyldimethyl-carboxymethylbetaine, lauryl-bis-(2-hydroxyethyl)carboxymethylbetaine, stearyl-bis-(2-hydroxypropyl)carboxymethylbetaine, oleyldimethyl-gamma-carboxypropylbetaine, lauryl-bis-(2-hydroxypropyl)alpha-carboxyethylbetaine, etc. The sulfobetaines may be represented by cocodimethylsulfopropylbetaine, stearyldimethylsulfopropylbetaine, lauryl-bis-(2-hydroxyethyl)sulfopropylbetaine, and the like.

Specific examples of amido betaines and amidosulfo betaines include the amidocarboxybetaines, such as cocamidopropyl betaine, cocamidodimethylcarboxymethylbetaine, laurylamidodimethylcarboxymethylbetaine, cetylamidodimethylcarboxymethylbetaine, laurylamido-bis-(2-hydroxyethyl)-carboxymethylbetaine, cocamido-bis-(2-hydroxyethyl)-carboxymethylbetaine, etc. The amido sulfobetaines may be represented by cocamidodi methylsulfopropylbetaine, stearylamidodimethylsulfopropylbetaine, laurylamido-bis-(2-hydroxyethyl)-sulfopropylbetaine, and the like.

Nonionic surfactants include those compounds produced by condensation of alkylene oxide groups, hydrophilic in nature, with an organic hydrophobic compound, which may be aliphatic or alkyl aromatic in nature. The nonionic surfactants include, but are not limited to (1) polyethylene oxide condensates of alkyl phenols, e.g., the condensation products of alkyl phenols having an alkyl group containing from about 6 to about 20 carbon atoms in either a straight chain or branched chain configuration, with ethylene oxide, the said ethylene oxide being present in amounts equal to from about 10 to about 60 moles of ethylene oxide per mole of alkyl phenol;

(2) those derived from the condensation of ethylene oxide with the product resulting from the reaction of propylene oxide and ethylene diamine products;

(3) long chain tertiary amine oxides of the formula $[R_1R_2R_3N{\rightarrow}O]$ where $R_1$ contains an alkyl, alkenyl or monohydroxy alkyl radical of from about 8 to about 18 carbon atoms, from 0 to about 10 ethylene oxide moieties, and from 0 to about 1 glyceryl moiety, and $R_2$ and $R_3$ contain from about 1 to about 3 carbon atoms and from 0 to about 1 hydroxy group, e.g., methyl, ethyl, propyl, hydroxyethyl, or hydroxypropyl radicals;

(4) long chain tertiary phosphine oxides of the formula $[RR'R''P{\rightarrow}O]$ where R contains an alkyl, alkenyl or monohydroxyalkyl radical ranging from about 8 to about 18 carbon atoms in chain length, from 0 to about 10 ethylene oxide moieties and from 0 to 1 glyceryl moieties and R' and R" are each alkyl or monohydroxyalkyl groups containing from about 1 to about 3 carbon atoms;

(5) long chain dialkyl sulfoxides containing one short chain alkyl or hydroxy alkyl radical of from 1 to about 3 carbon atoms (usually methyl) and one long hydrophobic chain which include alkyl, alkenyl, hydroxy alkyl, or keto alkyl radicals containing from about 8 to about 20 carbon atoms, from 0 to about 10 ethylene oxide moieties and from 0 to 1 glyceryl moieties; and (6) alkyl polysaccharide (APS) surfactants (e.g. alkyl polyglycosides) having a hydrophobic group with about 6 to about 30 carbon atoms and a polysaccharide (e.g., polyglycoside) as the hydrophilic group; optionally, there can be a polyalkylene-oxide group joining the hydrophobic and hydrophilic moieties; and the alkyl group (i.e., the hydrophobic moiety) can be saturated or unsaturated, branched or unbranched, and unsubstituted or substituted (e.g., with hydroxy or cyclic rings).

(7) The select ethoxylated fatty alcohols having an ethylene oxide moiety corresponding to the formula $(OCH_2CH_2)_n$, wherein n is from about 5 to about 150, preferably from about 6 to about 31, and more preferably from about 7 to about 21 moles of ethoxylation. Moreover, the ethoxylated fatty alcohols useful herein are those having a fatty alcohol moiety having from about 6 to about 30 carbon atoms, preferably from about 8 to about 22 carbon atoms, and more preferably from about 10 to about 19 carbon atoms. These fatty alcohols can be straight or branched chain alcohols and can be saturated or unsaturated. Examples of suitable ethoxylated fatty alcohols for use in cleansing compositions include ethoxylated fatty alcohols derived from coconut fatty alcohols, the ceteth series of compounds such as ceteth-5 through ceteth-45, which are ethylene glycol ethers of cetyl alcohol, wherein the numeric designation indicates the number of ethylene oxide moieties present; the steareth series of compounds such as steareth-5 through steareth-100, which are ethylene glycol ethers of steareth alcohol, wherein the numeric designation indicates the number of ethylene oxide moieties present; the laureth series of compounds such as laureth-5 through laureth-40, which are ethylene glycol ethers of lauryl alcohol, wherein the numeric designation indicates the number of ethylene oxide moieties present; ceteareth 5 through ceteareth-50, which are the ethylene glycol ethers of ceteareth alcohol, i.e. a mixture of fatty alcohols containing predominantly cetyl and stearyl alcohol, wherein the numeric designation indicates the number of ethylene oxide moieties present; $C_6$-$C_{30}$ alkyl ethers of the ceteth, steareth, and ceteareth compounds just described; the pareth series of compounds such as pareth-5 through pareth-40, which are ethylene glycol ethers of synthetic fatty alcohols containing both even- and odd-carbon chain length fractions, wherein the numeric designation indicates the number of ethylene oxide moieties present; and mixtures thereof. Specific examples of ethoxylated fatty alcohols are those selected from the group consisting of ceteth-10, ceteth-20, steareth-10, steareth-20, steareth-21, steareth-100, laureth-12, laureth-23, ceteareth-20, C12-13 pareth-7, C12-15 pareth-9, C14-15 pareth-13, and mixtures thereof.

(8) Alkoxylated alkanolamides such as $PPG_2$ hydroxyethyl cocamide (Promidium CO, available from Uniqema), $PPG_1$, hydroxyethyl caprylamide (Promidium CC, available from Uniqema), $PPG_{1.5}$ hydroxyethyl isostearamide, $PPG_3$ hydroxyethyl soyamide (Promidium SY, available from Uniqema), PPG-2 hydroxyethyl coco/isostearamide (Promidium-2 available from Uniqema).

Frequently used surfactants include amine oxides, polyhydroxy fatty acid amides, ethoxylated alkyl sulfates, alkyl ethoxylates, alkyl sulfates, alkylbenzene sulfonates, alkyl ether carboxylates, alkyl glycosides, methyl glucose esters, and betaines, such as sodium lauryl sulfate, sodium laureth sulfate, ammonium lauryl sulfate, ammonium lauryl ether sulfate, secondary $C_{14-17}$ alkane sulfonates (SAS),2-($C_{14}$-$C_{16}$)alkene sulfonate, 3-($C_{14}$-$C_{16}$)hydroxy ($C_{14}$-$C_{16}$)alkene sulfonate, 4-hydroxyalkene sulfonate, cocoamidopropyl betaine, alkoxylated alkanolamides, and combinations thereof.

EXAMPLES

Formula 3 and Table 3 provide a summary of the polysiloxane compositions of the examples.

lateral (pendant) amino functional silicone fluid having an average molecular weight (per primary amine) of about 4400 obtained from Shin-Etsu under the product designation of KF-865. 88 grams (0.02 moles) of the silicone fluid was admixed with 2.6 grams of itaconic acid (0.02 moles) and heated to a temperature of 120° C. to obtain a clear melt. The heating was continued for an additional two hours, with the product formed having an acid number of 13 mg potassium hydroxide per gram, molecular weight average (Mw) of about 20,000 and molecular weight number average (Mn) of about 7500. This material is commercially available as Monasil PCA, (Uniqema, New Castle, Del.)

Example 2

100.0 grams (0.05 moles) of a lateral (pendant) amino functional silicone fluid having an average molecular weight (per primary amine) of about 2250 and as otherwise described in Table 1 was admixed with 6.5 grams of itaconic acid (0.05 moles) and heated to a temperature of 120° C. to obtain a clear melt. The heating was continued for an additional two hours, with the product formed having an acid number of 28 mg potassium hydroxide per gram, average molecular weight (Mw) of about 40,000 and molecular weight number average (Mn) of about 20,000.

Example 3

100.0 grams (0.045 moles) of a lateral amino functional silicone fluid having an average molecular weight (per primary amine) of about 2300 and as otherwise described in Table 1 was admixed with 5.6 grams of itaconic acid (0.045 moles) and heated to a temperature of 120° C. to obtain a clear melt. The heating was continued for an additional two hours, with the product formed having an acid number of 26 mg potassium hydroxide per gram, average molecular weight (Mw) of about 50,000 and molecular weight number average (Mn) of about 30,000.

TABLE 1

| | Aminopolysiloxane | | | Amidopolysiloxane | | | Acid |
| Ex | X | $M_w$* | $M_n$* | X | $R^2$ | a:b | Eq Wt |
| --- | --- | --- | --- | --- | --- | --- | --- |
| 1 | —$NH_2$ | 20,000 | 7,500 | | Me | 66:1 | 4400 |
| 2 | —$NH_2$ | 40,000 | 20,000 | | Me | 25.4:1 | 2250 |
| 3 | —$NH_2$ | 50,000 | 30,000 | | Me w/40% | 25.6:1 | 2300 |
| 4 | —$NH_2$ | 3000 | 910 | | EtO | 4.5:1 | 450 |
| 5 | —$NH_2$ | 10000 | 3400 | | Me Me | 29.4:1 | 2410 |

*$M_w$ and $M_n$ of the aminopolysiloxane starting material.

Example 1

The pyrrolidone carboxy substituted polysiloxane of Example 5 of U.S. Pat. No. 5,807,955 was prepared using

Example 4

100.0 grams (0.22 moles) of a lateral (pendant) amino functional silicone fluid having an equivalent weight (per primary amine) of about 450 and as otherwise described in Table 1 was obtained and admixed with 28.0 grams of itaconic acid (0.22 moles) and heated to a temperature of 120° C. to obtain a clear melt. The heating was continued for an additional two hours, with the product formed having an acid number of 128 mg potassium hydroxide per gram, an average molecular weight Mw of about 3000 and a molecular weight number average (Mn) of about 900. The prepared material was not soluble in water.

Example 5

100.0 grams (0.05 moles) of a lateral (pendant) amino functional silicone fluid having an equivalent weight (per primary amine) of about 2000 and as otherwise described in Table 1 was admixed with 6.5 grams of itaconic acid (0.05 moles) and heated to a temperature of 120° C. to obtain a clear melt. The heating was continued for an additional two hours, so the reaction temperature did not drop more than 3° C. during addition. In these examples the ITA solution was added in increments with two-thirds being added first and reacted for 10 minutes and then the viscosity was tested. When the viscosity was in the range 300 to 1000 cPs at 50° C., the next addition of one-ninth of the ITA solution was added and reacted for 10 minutes. Then the viscosity was tested and when it was in the range 1000 to 1300 cPs at 50° C., then the next one-ninth portion of the ITA solution was added over 30 minutes and reacted for another 10 minutes before measuring the viscosity again. When the viscosity was in the range of 1300 to 1500 cPs at 50° C., the last one-ninth of the ITA solution was added over 30 minutes. After the viscosity is in the range of 1500 to 1200 cPs at 50° C., the mixture is held at reaction temperature and sampled every two hours for viscosity, acid value and alkali number until meeting desired specifications. It is then allowed to cool to about 50° C. and filtered.

TABLE 2

| Ex | Starting Amino Silicone | Silicone Amine # | Moles of Primary Amine | Moles Itaconic Acid | Solvent | Solvent Mass | % Unreacted Amine | Final Acid # | 1 or 2 Phase |
|---|---|---|---|---|---|---|---|---|---|
| 6 | Same as Ex. 5 | 25.60 | 0.077 | 0.075 | D5♦ | 178.60 | 1.37 | 11.90 | 1 |
| 7 | Same as Ex. 5 | 25.60 | 0.077 | 0.075 | Isopar M* | 178.60 | 1.21 | 12.10 | 1 |
| 8 | Same as Ex. 4 | 137.10 | 0.333 | 0.333 | D5 | 177.90 | <1% | 53.30 | 1 |
| 9 | Same as Ex. 4 | 137.10 | 0.333 | 0.326 | Isopar M | 179.00 | <1% | 57.00 | 2 |
| 10 | Same as Ex. 1 | 28.00 | 0.083 | 0.084 | D5 | 177.90 | <1% | 13.50 | 1 |
| 11 | Same as Ex. 1 | 28.00 | 0.083 | 0.084 | Isopar M | 177.90 | <1% | 13.80 | 1 |

♦$D^5$ is cyclopentadimethicone and is of medium polarity
*Isopar M is a branched isoparaffinic hydrocarbon solvent by ExxonMobil which is fairly non-polar.

with the product formed having an acid number of 28 mg potassium hydroxide per gram polysiloxane, an average molecular weight (Mw) of about 10,000 and a molecular weight number average (Mn) of about 3300.

Examples 6-11

Additional pyrrolidone-carboxylic modified polysiloxanes were made. The materials, solvents and amounts are shown in Table 2. The itaconic acid solution used in these examples was prepared by adding itaconic acid (ITA) to excess isopropanol and heating to about 40° C. to 50° C. until the ITA was dissolved into the alcohol, then allowed to cool. The itaconic acid was dissolved in isopropanol (IPA) at 50° C. to give a 15% weight/weight active solution, equating to 55.15 g IPA The amount of the ITA that was added was based on the amount and alkali number of the polysiloxane starting material according to the following formula:

$$\text{Itaconic Acid (g)} = \frac{[\text{aminopolysiloxane starting material (g)} \cdot \text{aminopolysiloxane alkali number}]}{[ITA \text{ acid value} \cdot 2]}.$$

(Since water generated by the reaction counts only 0.2% of the total charge, it was ignored from the percent solid calculation.)

The amino polysiloxane starting material was charged to the reactor and then the solvent was added and the agitator started. The cooling water on reflux condenser was turned on and the reactor slowly heated to 85° C.±5° C. Once at reaction temperature, the ITA solution was added slowly in a manner Example 9 illustrates the importance of matching the polarity of the solvent with the final product. In this example, the product is too polar due to a high incorporation of pyrrolindone carboxylate to remain in phase with the isoparaffinic solvent upon cooling. Polar solvents, such as $C_{6-12}$ alkyl esters of lower alcohols or lower alcohols would be preferred and also enhances reaction rates.

Example 12

A premix was obtained where itaconic acid was dissolved in isopropanol (IPA) at 50° C. to give a 15% weight/weight active solution, equating to 55 g IPA. Thereafter, the quantity of solvent required to give a 50% weight/weight active final product was calculated and shown in Table 3.

Charged to a reaction flask was 150 g of an aminosilicone starting material the same as that used for Example 2 of Table 1. Its amine value was calculated to determine the amount of itaconic acid needed for a stoichiometric reaction. In this example, the starting aminopolysilicone had a measured amine value of 28 mg KOH/g, then 150 g contains 0.07487 moles of amine which equates to 9.73 g of itaconic acid.

Then 105 g isopropanol was added to the aminosilicone in the reactor as solvent and brought to a reaction temperature of 86° C. At reaction temperature, the itaconic acid/IPA premix was slowly added over about one hour via drip feed yielding 160 g total IPA solvent under reflux.

The reaction was monitored via acid and amine values until the reaction reached the desired end point of less than 1% remaining amine. At this stage, the heat was removed and the reaction cooled to room temperature. A total of 10 hours under reflux was required.

Example 13 was made using the same general process using the materials and conditions described in Table 3, except isopropyl myristate (IPM) was used as part of the solvent system to raise reflux temperature and lower reaction time to 6 hours.

Example 14 uses IPA as solvent in a closed reflux at 2 Bar gauge pressure to further reduce reaction cycle time.

TABLE 3

| Ex. | Amino Silicone (g) | Itaconic Acid (g) | IPM Solvent (g) | IPA Solvent (g) | Reaction Temp ° C. | ITA Soln Addition Time (hr) | Total Reaction Time (hr) |
|---|---|---|---|---|---|---|---|
| 12 | 150 | 9.73 | 0 | 160 | 86 | 1 | 10 |
| 13 | 151 | 9.8 | 102 | 55 | 100 | 1 | 6 |
| 14 | 150 | 9.7 | 0 | 160 | 115 | 1 | 4* |

*at 2 BarG pressure

Example 15

Failed Emulsion Using a Carboxy-Polysiloxane of the Prior Art

Oil Phase preparation: One gram of the trimethylsiloxy capped polysiloxane product of Example 1 was gently mixed for one hour at room temperature with 19 grams decamethylcyclopentasiloxane. Water phase preparation: 0.70 grams of magnesium sulfate was dissolved in 78.30 grams distilled water.

The water phase was combined slowly to the oil phase under moderate homogenization (2000 rpm), followed afterwards by 2-minute homogenization at 10,000 rpm. The product phase separated immediately.

Example 16

Emulsion

Oil Phase preparation: One gram of the trimethylsiloxy capped polysiloxane product of Example 2 was gently mixed for one hour at room temperature with 19 grams decamethylcyclopentasiloxane.

The water phase preparation and method of combining the two phases were as described in Example 15 above.

The resultant product was a low viscosity water-in-oil emulsion that showed no sign of phase separation after two weeks at 45° C. and was still stable after 6 months at 25° C.

Example 17

Same composition and method as Example 16 were used with the addition of 0.25 grams of glycolic acid to the water phase prior to emulsification. The product phase was a medium-viscosity (about 10,000 cPs) water-in-oil emulsion that showed no sign of phase separation after two weeks at 45° C. and was still stable after 6 months at 25° C.

Example 18

The following oil phase ingredients were combined at 25° C. and mixed completely.

TABLE 4

| Oil Phase Mixture | Grams |
|---|---|
| DC345 Cyclopenta siloxane fluid (D5) | 4.35 |
| Arlamol HD (isohexadecane) | 52.17 |

TABLE 4-continued

| Oil Phase Mixture | Grams |
|---|---|
| Arlamol E (PPG 15 stearyl ether) | 13.05 |
| Estol 1512 (Isopropyl Myristate) | 30.43 |

This oil phase was then combined with carboxy polysiloxane product of Example 2 polymer and blended together until uniform to make the Oil Phase A with Emulsifier shown in Table 5.

TABLE 5

Water in Mixed Silicone Fluid/Hydrocarbon Oil Emulsion

| | Grams |
|---|---|
| A: Oil Phase with Emulsifier | |
| Oil Phase Mixture, above | 19.0 |
| Silicone Polymer from Example 2 | 1.0 |
| B: Water Phase Premix | |
| DI water at pH 5.5 | 74.8 |
| MgSO4•7H2O | 0.2 |
| Glycerine | 4.0 |
| Germaben II | 1.0 |

The components of water phase B of Table 5 were added together and mixed until clear. The water phase was combined slowly to the oil phase under moderate (2000 rpm) homogenization, followed afterwards by 2-minute homogenization at 10,000 rpm resulting in a water-in-oil emulsion that was still stable after five freeze-thaw cycles of −20° C. and 25° C.

Example 19

A water-in-oil organic-class sunscreen emulsion was prepared with a sample of the trimethylsiloxy capped polysiloxane fluid of Example 2.

TABLE 6

Water in Mixed Silicone Fluid/Hydrocarbon Oil Emulsion

| | Grams |
|---|---|
| A: Oil Phase with Emulsifier | |
| Example 18 oil phase mixture | 12.0 |
| Silicone Polymer from Example 2 | 1.0 |
| Benzophenone-3 | 5.0 |
| Finsolv TN (Mixed Alkyl Benzoate ester) | 2.0 |
| B: Water Phase Premix | |
| DI water at pH 5.5 (HCl) | 72.0 |
| MgSO4•7H2O | 1.0 |
| Glycerine | 4.0 |
| Propylene glycol | 2.0 |
| Germaben II (Preservative) | 1.0 |

The water phase was combined into the oil phase using the method described in Example 18 above. A stable, pseudoplastic (thickened) cream with good sensory properties was obtained.

Example 20

A water-in-oil emulsion with organic sunscreen in both aqueous and oil phases was prepared with a sample of the trimethylsiloxy capped polysiloxane fluid of Example 2.

TABLE 7

Water in Mixed Silicone Fluid/Hydrocarbon Oil Emulsion

| | Grams |
|---|---|
| Part A: Oil Phase with Emulsifier | |
| D5 | 13.0 |
| Example 2 polymer | 1.0 |
| Benzophenone-3 | 2.5 |
| Finsolv TN (Mixed Alkyl Benzoate ester) | 3.5 |
| Part B: Water Phase Premix | |
| Parsol* HS (Roche Vitamins) | 2.5 |
| DI water at pH 5.5 (HCl) | 69.5 |
| MgSO$_4$•7H$_2$O | 1.0 |
| Glycerine | 4.0 |
| Propylene glycol | 2.0 |
| Preservative (Germaben II) | 1.0 |

*Parsol is butylmethoxydibenzoylmethane.

The water phase was combined to the oil phase using the method described in Example 18 above. A stable, pseudoplastic (thickened) cream with good sensory properties is obtained.

Example 21

An antiperspirant/deodorant-type composition was prepared by first combining the oil phase mixture of Example 18 with Example 4 polymer product and blending together until uniform to make the oil phase A with emulsifier; followed by combining the components of water phase B and mixing until uniform; after which the water phase was combined to the oil phase using the method described in Example 18 above.

TABLE 8

Water in Mixed Silicone Fluid/Hydrocarbon Oil Deodorant Emulsion

| | Grams |
|---|---|
| A: Oil Phase with Emulsifier | |
| Example 18 oil phase mixture | 19.7 |
| Silicone Polymer from Example 4 | 0.3 |
| B: Water Phase Premix | |
| Deionized water | 74.8 |
| Aluminum Zirconium Glycinate Salt (Westwood) | 13.0 |

The emulsion product viscosity was in the same range as that generally found in commercial roll-on products. The emulsion product was stable for more than six months at room temperature and illustrates that even low amounts of polymer can greatly impact stability. The same formulation was made without the polymer and it immediately separated.

Example 22

Translucent antiperspirant compositions were prepared by first combining the silicone oil with equal parts of Example 1 and Example 4 polymers and blending together until uniform to make the oil phase A.

The ingredients of water phase B were blended and homogenized until uniform. Both phases were heated to about 50° C. after which the water phase was combined to the oil phase using the method described in Example 18 above (while observing it thickened dramatically and became clear). Both example products cooled to a stable translucent paste. These examples are not considered optimized in terms of clarity and it is anticipated that additional refractive index matching, as known to those in the art, will yield a clear product at room temperature. The translucent emulsion appeared clear and non-whitening when applied to the skin.

TABLE 9

Antiperspirant Translucent Gel Emulsion Formulations

| | 22 Grams | 23 Grams |
|---|---|---|
| A: Oil Phase | | |
| Cyclopentadimethicone (D5) | 20.0 | 20.0 |
| Example 1 Polymer | 0.75 | 0.75 |
| Example 2B Polymer | 0.75 | 0.75 |
| B: Water Phase | | |
| Tween-80 | 0.25 | 0.25 |
| Glycerol | 3 | 3 |
| Propylene glycol | 12 | 12 |
| Aluminum Zirconium Glycinate Salt Reach AZP-90B (Reheis) | 20 | 30 |
| DI water (deionized water) | 43.25 | 33.25 |

Example 24

A water-in-oil emulsion lubricating polish with no volatile organic components (zero VOC, Volatile Organic Compound) was prepared using the techniques described in the emulsion examples above. PDMS in Table 10 refers to polydimethylsiloxane which provide the lubricant polish properties.

TABLE 10

Water in Mixed Low/High Viscosity Silicone Fluid Emulsion

| | Grams |
|---|---|
| A: Silicone Fluids with Emulsifier | |
| D5 (cyclopentadimethicone) | 12 |
| 350 cSt PDMS fluid (DC-200)* | 4 |
| 1000 cSt PDMS fluid (DC-200) | 2 |
| 10,000 cSt PDMS fluid (DC-200) | 1 |
| Example 4 polymer | 1 |
| B: Water Phase | |
| Deionized water | 74 |
| MgSO4 | 1 |
| Glycerol | 4 |
| Preservative (Germaben II) | 1 |

*Trademark of Dow Corning.

The emulsion broke easily when polishing hard surfaces and therefore was considered easy to apply. It beaded water, was free of attracted dirt and was still extremely glossy and smooth a month later. It is felt that this class of emulsions would be useful in many polish and/or lubricant applications, particularly those related to the automotive, metalworking, furniture and hard surface industries.

Example 25

A test cleanser was prepared by blending together the ingredients listed in Table 11.

TABLE 11

| TEST CLEANSER | SOURCE | ACTIVE |
|---|---|---|
| Sodium Laureth Sulfate | Standapol ES-2, Cognis | 9.0% |
| Sodium Lauryl Sulfate | Standapol WAQ-LC, Cognis | 5.0% |
| Monateric CAB-L | Uniqema | 2.0% |
| Promidium 2 Surfactant | Uniqema | 2.0% |
| Water | | 81.5% |
| Citric Acid to adjust pH 6 | | |
| Sodium Chloride | | 0.5% |

20% by weight of the active polymer from Example 4 (acid equivalent weight of 450 g/mol) was blended with deionized water to prepare a two-phase dispersion. This dispersion was then neutralized with NaOH (inorganic), TEA (very hydrophilic) or cocodimethyl amine (CDA) (moderate hydrophobe) to ~pH 6, followed by blending each with a portion of the test cleanser as indicated in Table 12 below. The stability of the resultant test cleansers were observed and reported in Table 12.

TABLE 12

| Solubility in Test Cleanser | | | | | |
|---|---|---|---|---|---|
| Blends (in grams) | | | Readings | | |
| % Cleanser | % Polymer Active | | 25° C. | 5° C. | Krafft Point |
| Ex. 4 Polymer w/NaOH | | | | | |
| 0.00 | 10 (control) | 0 | Clear | Clear | <5° C. |
| 0.10 | 9.90 | 0.2 | Clear | Clear | <5° C. |
| 0.50 | 9.50 | 1.0 | Clear | Clear | <5° C. |
| Ex. 4 Polymer w/TEA | | | | | |
| 0.10 | 9.90 | 0.2 | Clear | Clear | <5° C. |
| 0.50 | 9.50 | 1.0 | Clear | Clear | <5° C. |
| Ex. 4 polymer w/CDA | | | | | |
| 0.50 | 9.50 | 10.00 | Clear | Clear | <5° C. |
| 0.50 | 9.50 | 10.00 | Clear | Clear | <5° C. |

All pH adjusted with citric acid.

Regardless of the ion pair or salt formed, the amidopolysiloxane of the present invention from example 4 is completely compatible in the cleanser system and was noted to foam well, in contrast to the silicone polymers in the art which act as defoamers.

Example 26

25% isopropyl myristate by weight was added to 75% by weight Example 2 polymer to slightly dilute the polymer such that the viscosity was reduced. This mixture was mixed in a 50:50 by weight ratio with SLES-2 (a hydrophobic surfactant of sodium laureth-2 sulfate) and then neutralized to pH 6 with NaOH (38% final polymer activity). The product was thin and clear prior to neutralization but formed a clear gel after NaOH neutralization. The non-neutralized mixture was clear and easy to handle, so it was selected for use, Part II of Table 13, in the next example.

Example 26A-D

The sample of example 26 was added to the test cleanser, but the process was slow and difficult due to low dissolution time of the silicone polymer in the cleanser. Consequently, the order of addition was altered by making the cleanser base with only the surfactants, thus leaving out the final water charge until after the polymer premix was added. Thus, the Surfactant Premix, Part I, and the Polymer Addition, Part II, of Table 13 were blended and the water, salt and pH of Part III were then added with mixing. For each sample, Parts, I, II and III were blended in the amounts provided in Table 14.

TABLE 13

| Test Cleanser, new order of addition | Active Basis (wt. %) | Actual amount (g) | Actual water (g) |
|---|---|---|---|
| Part I - Surfactant premix | | | |
| Sodium Laureth Sulfate (Standapol ES-2, from Cognis) | 9.0 | 34.61 | 25.61 |
| Sodium Lauryl Sulfate (Standapol WAQ-LC, from Cognis) | 5.0 | 17.24 | 12.24 |
| Monateric CAB-LC (from Uniqema) | 2.0 | 5.71 | 3.71 (incl. NaCl) |
| Promidium 2 surfactant (from Uniqema) | 1 | 1 | 0 |
| Part II - Polymer addition | | | |
| Example 26 (50:50 Polymer:SLES Premix) (38% active polymer) | 0 to 10 | 0-4.4 | |
| Part III (finish) | | | |
| Water | qs | qs to 100 g | |
| Citric Acid or NaOH to final adjust pH 5.8-5.9 | qs | 0.1 | |
| Sodium Chloride | 0.7 | 0.7 | |

TABLE 14

| Formula | Part I (g) | Part II (g) | Part III (g) | Active silicone polymer (wt. %) | 25° C. Appearance/ Turbidity | Krafft Point |
|---|---|---|---|---|---|---|
| Example 26A | 6.00 | 0.26 | 4.0 | 1.0 | Clear <10 NTU | <5° C. |
| Example 26B | 6.00 | 0.53 | 4.0 | 1.9 | Clear <10 NTU | <5° C. |
| Example 26C | 6.00 | 0.79 | 4.0 | 2.8 | Clear <10 NTU | <5° C. |
| Example 26D | 6.00 | 1.32 | 4.0 | 4.4 | Clear <10 NTU | <5° C. |

All pH's adjusted to ~6.5
No salt added
Turbidity can be an appearance ranking (cloudy or clear) or a standardized number in NTU's (Nephelometric turbidity unit).

Even at over 4% polymer by weight, the clarity was surprisingly clear. This result compares very favorably considering most commercial silicone polymers are low molecular weight (~750-1000 daltons) and typically highly ethoxylated to achieve this result. Cleansing and foaming were good and the product left a desirable conditioned feel to the hands, without any feel of product build-up.

Using the industry standard Ross Miles Foam test at 40° C., the formulation of 26A was tested against a control (same formulation without the polysiloxane of Example 2). The foam reported density (in millimeters, m) given below was obtained by taking the actual foam height and subtracting from it the drainage liquor of 50-70 mm (millimeters).

| | Time (minutes) | | |
|---|---|---|---|
| Formulation | 0 | 1 | 5 |
| Control | 260 mm | 230 mm | 227 mm |
| Ex. 2 polymer at 1% | 220 mm | 200 mm | 195 mm |

The amidopolysiloxane of Example 2 can be simply formulated in a clear cleansing system without greatly impacting foam. The alkalinity of the surfactants tended to self-neutralize the amidopolysiloxane.

What is claimed is:

1. A 2-pyrrolidone-4-carboxylic substituted polysiloxane represented by the random polymer of Formula 1 comprising:

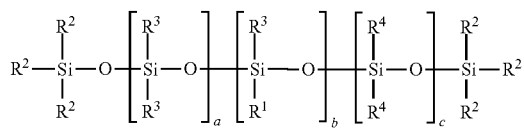

wherein:
$R^1$ is a pyrrolidone-containing functional group as shown in Formula 2:

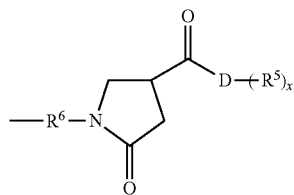

D is oxygen or nitrogen, wherein at least 50% on a molar basis of D is oxygen;
$R^5$ is hydrogen, $(C_1-C_{22})$ alkyl or polyoxy $(C_2-C_3)$ alkylene of 2 to 200 units, wherein at least 50% on a molar basis of $R^5$ is hydrogen
x is 1 or 2;
$R^6$ is branched or unbranched $(C_{1-20})$ alkyl;
$R^2$ independently selected from $(C_1-C_4)$ alkyl, phenyl or —$OR^7$, wherein $R^7$ is hydrogen or $(C_{1-6})$ alkyl;
$R^3$ independently selected from $(C_1-C_4)$ alkyl or phenyl;
$R^4$ independently selected from phenyl, $(C_{1-36})$ alkyl, $(C_{1-36})$ alkenyl, and/or $(C_{1-20})$ alkyl-capped or uncapped polyoxy $(C_2-C_3)$ alkylene of 2 to 200 units;
a is an integer from 10 to 560;
b is an integer from 1 to 40, wherein the absolute ratio of a to b is about 2.5 to about 35 and wherein the average integer sum of a+b exists in the range of 11 to 600; and
c is an integer from 0 to 10, wherein the absolute ratio of b to c is no less than about 4;
wherein the polysiloxane of Formula 1 comprises:
i) a detergent solubility of up to 50 wt %; and/or
ii) an aqueous solubility of up to 50 wt %.

2. The polysiloxane composition of claim 1 wherein $R^1$, the pyrrolidone-containing functional group, D is oxygen;
$R^5$ is hydrogen, $(C_1-C_6)$ alkyl or a polyoxy $(C_2-C_3)$ alkylene of 1 to 6 units;
$R^6$ is a branched or unbranched $(C_3-C_4)$ alkyl;
each $R^2$ is selected from methyl, phenyl, —$OR^7$ where $R^7$ is methyl, ethyl or hydrogen, and wherein collectively $R^2$ is substantially capped;
each $R^3$ is selected from methyl or phenyl;
each $R^4$ is selected from phenyl, methyl, $(C_{1-36})$alkyl, or $(C_{1-20})$alkyl-capped or uncapped polyoxy$(C_2-C_3)$alkylene of 2 to 30 units;
a is an integer from 10 to 560;
b is an integer from 1 to 40, wherein the absolute ratio of a to b is about 2.5 to about 35;
and the average integer sum of a+b exists in the range 11 to about 400,
c is an integer from 0 to 10, and
the absolute ratio of b to c is no less than about 4.

3. The polysiloxane composition of claim 2 wherein:
$R^2$ is methyl; $R^3$ is methyl; $R^5$ is hydrogen; D is oxygen; $R^6$ is propyl or isobutyl;
a is an integer from 10 to 560; b is an integer from 1 to 40, wherein the absolute ratio of a to b is about 2.5 to about 35, and the average integer sum of a+b exists in the range of about 150 to about 350; and
c is 0.

4. The polysiloxane composition of claim 1 wherein the absolute a to b ratio is about 2.5-35 and from about 1-100 percent on a molar basis of the carboxyl groups, formed from the D and $R^5$ substituents, are neutralized rendering the polysiloxane composition detergent soluble.

5. The composition of claim 1 wherein the absolute a to b ratio is about 13-33 and from about 50-100 percent on a molar basis of the carboxyl groups, formed from the D and $R^5$ substituents, are neutralized to a solution pH of about 3.5-11.

6. The composition of claim 2 wherein the absolute a to b ratio is about 13-33 and from about 50-100 percent on a molar basis of the carboxyl groups, formed from the D and $R^5$ substituents, are neutralized to a solution pH of about 4.5-8.

7. The composition of claim 6 wherein $R^6$ is propyl and the a to b ratio is about 20-26.

8. A polysiloxane composition comprising:
i) about 0.1 to 10 weight percent of the polysiloxane of claim 4;
ii) 90-99.9 percent by weight of a detergent system wherein the detergent is selected from anionic, cationic, non-ionic, amphoteric surfactants, and mixtures thereof that form a single clear phase in water, wherein the surfactants comprise about 5 weight percent to 50 weight percent of the detergent system.

9. A polysiloxane composition comprising:
i) about 0.5 to 5 weight percent of the polysiloxane of claim 6;
ii) about 95-99.5 percent by weight of a detergent system wherein the detergent is selected from anionic, cationic, non-ionic, amphoteric surfactants, and mixtures thereof that form a single clear phase in water, wherein the detergent comprises about 5 weight percent to 50 weight percent of the detergent system.

10. The polysiloxane composition of claim 9 wherein the polysiloxane has an absolute a:b ratio of about 20-26.

11. The polysiloxane composition of claim 9 wherein the detergent is selected from the group consisting of amine oxides, lauryl sulfate and its cationic salts, laureth sulfate and its cationic salts, 2-$(C_{14}-C_{16})$ alkene sulfonate and its cationic salts, 3-hydroxy $(C_{14}-C_{16})$ alkene sulfonate and its cationic salts, 4-hydroxy $(C_{14}-C_{16})$ alkene sulfonate and its cationic salts, cocoamidopropyl betaine, amine oxides, secondary alkane sulfonates, alkoxylated alkanolamides and combinations thereof.

12. The polysiloxane composition of claim 11 wherein the detergent is selected from the group consisting of sodium lauryl sulfate, sodium laureth sulfate, ammonium lauryl sulfate, ammonium lauryl ether sulfate, sodium 2-($C_{14}$-$C_{16}$) alkene sulfonate, sodium 3-hydroxy ($C_{14}$-$C_{16}$) alkene sulfonate, sodium 4-hydroxy ($C_{14}$-$C_{16}$) alkene sulfonate, cocoamidopropyl betaine, and combinations thereof; the detergent comprises about 5 to 50 weight percent of the detergent system; and the absolute ratio of a to b of the polysiloxane is about 20-26.

13. The polysiloxane composition of claim 12 wherein $R^6$ is propyl and the polysiloxane has a weight average molecular weight of about 15,000-25,000 daltons.

14. The polysiloxane composition of claim 1 wherein the absolute a to b ratio is about 2.5-13 and from about 50-100 percent on a molar basis of the carboxyl groups, formed from the D and $R^5$ substituents, are neutralized rendering the polysiloxane composition water-soluble.

15. The composition of claim 2 wherein the absolute a to b ratio is about 2.5-13 and from about 50-100 percent on a molar basis of the carboxyl groups, formed from the D and $R^5$ substituents, are neutralized rendering the polysiloxane composition water-soluble.

16. A polysiloxane composition comprising
    i) about 0.1 to 10 weight percent of the polysiloxane of claim 14; and
    ii) 90-99.9% by weight of a clear aqueous system comprised primarily of water and other optional water-soluble additives.

17. A polysiloxane composition comprising
    i) about 0.5 to 5 weight percent of the polysiloxane of claim 15; and
    ii) 95-99.5% by weight of a clear aqueous system comprised primarily of water and other optional water-soluble additives.

18. A polysiloxane containing water-in-oil emulsion comprising:
    (a) about 0.1 to about 5 weight/weight percent of an polysiloxane composition of claim 2 wherein the absolute ratio of a to b is about 13-35;
    (b) about 18 to about 50 weight/weight percent of an oil phase selected from silicone oil, hydrocarbon oil and mixtures thereof; and
    (c) about 50 to about 90 weight/weight percent of a water phase having a solution pH of about 2 to about 12, with about 0.1 to about 40 weight percent added electrolyte.

19. The polysiloxane composition of claim 3 wherein the absolute ratio of a to b is about 15-33 and the weight average molecular weight Mw is about 15,000-25,000 daltons.

20. The water-in-oil emulsion of claim 18 further comprising the polysiloxane of claim 3 having an absolute ratio of a to b of about 20-26 and a weight average molecular weight Mw of about 15,000-25,000 daltons.

21. The water-in-oil emulsion of claim 18 wherein the oil phase comprises from about 20-40 weight percent of the emulsion, the oil is selected from cyclomethicones, cycloalkylmethicones, liquid triglycerides, ($C_6$-$C_{18}$)alkyl esters of ($C_1$-$C_6$)alcohols and mixtures thereof; and the polysiloxane composition comprises about 0.25-2 weight percent of the emulsion.

22. The emulsion of claim 21 further comprising as part of the water phase aluminium zirconium salts.

23. The emulsion of claim 21 further comprising a sunscreen.

24. A process for making a polysiloxane composition comprising a 2-pyrrolidone-4-carboxylic substituted polysiloxane represented by the random polymer of Formula 1 comprising:

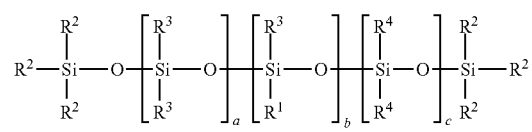

wherein:
R$^1$ represents a pyrrolidone-containing functional group as shown in Formula 2:

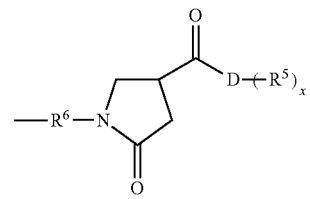

D represents oxygen or nitrogen, wherein at least 50% on a molar basis of D is oxygen;
$R^5$ represents hydrogen, ($C_1$-$C_{22}$) alkyl or polyoxy ($C_2$-$C_3$) alkylene of 2 to 200 units, wherein at least 50% on a molar basis of $R^5$ is hydrogen;
x represents 1 or 2;
$R^6$ represents branched or unbranched ($C_{1-20}$) alkyl;
$R^2$ independently represents ($C_1$-$C_4$) alkyl, phenyl or —OR$^7$, wherein $R^7$ is hydrogen or ($C_{1-5}$) alkyl;
$R^3$ independently represents ($C_1$-$C_4$) alkyl or phenyl;
$R^4$ independently represents phenyl, ($C_{1-35}$) alkyl, ($C_{1-35}$) alkenyl, and/or ($C_{1-20}$) alkyl-capped or uncapped polyoxy($C_2$-$C_3$)alkylene of 2 to 200 units;
a represents an integer from 10 to 560;
b represents an integer from 1 to 40, wherein the absolute ratio of a to b is about 2.5 to about 35 and wherein the average integer sum of a+b is in the range of 11 to 600; and
c represents an integer from 0 to 10, wherein the absolute ratio of b to c is no less than about 4;
wherein the process to form the composition comprising the polysiloxane of Formula 1, comprising reacting, in the presence of a solvent system comprising a ($C_1$-$C_6$) alcohol and a ($C_6$-$C_{18}$) alkyl ester of a ($C_1$-$C_6$) alcohol, the following:
    A) itaconic acid; and
    B) an aminopolysiloxane of the formula:

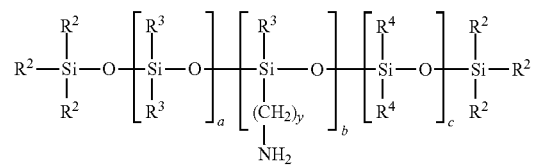

wherein:
i) $R^2$, $R^3$, $R^4$, a, b, and c are as described for the polysiloxane of Formula 1;
ii) $(-CH_2-)_y$ is a branched or unbranched alkylene group; and
iii) y is 1-20.

25. The process of claim 24, wherein the reaction is run at a temperature of about 90 to 110° C. for a reaction time of about two to three hours and the solvent system comprises an alcohol selected from isopropanol, propanol and mixtures thereof and an ($C_6$-$C_{18}$) alkyl ester selected from isopropyl myristate ester, isopropyl palmitate ester, isopropyl laurate ester and combinations thereof, and c is zero.

26. The process of claim 24, wherein the solvent system comprises a combination of isopropyl myristate and isopropanol at a ratio of 1:1 to 10:1 by weight.

27. A polysiloxane containing water-in-oil emulsion comprising:
i) about 0.25 to about 2 wt % of the emulsion comprises a polysiloxane composition comprising a 2-pyrrolidone-4-carboxylic substituted polysiloxane represented by the random polymer of Formula 1 comprising:

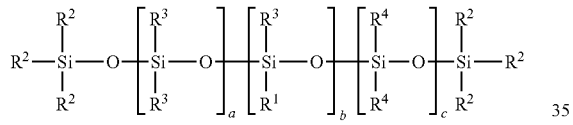

wherein:
$R^1$ represents a pyrrolidone-containing functional group as shown in Formula 2:

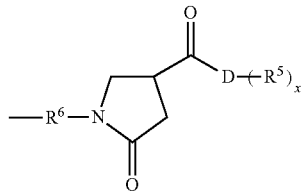

D represents oxygen or nitrogen, wherein at least 50% on a molar basis of D is oxygen;
$R^5$ represents hydrogen, ($C_1$-$C_{22}$) alkyl or polyoxy ($C_2$-$C_3$) alkylene of 2 to 200 units, wherein at least 50% on a molar basis of $R^5$ is hydrogen;
x represents 1 or 2;
$R^6$ represents branched or unbranched ($C_{1-20}$) alkyl;
$R^2$ independently represents ($C_1$-$C_4$) alkyl, phenyl or —$OR^7$, wherein $R^7$ is hydrogen or ($C_{1-6}$) alkyl;
$R^3$ independently represents ($C_1$-$C_4$) alkyl or phenyl;
$R^4$ independently represents phenyl, ($C_{1-36}$) alkyl, ($C_{1-36}$) alkenyl, and/or ($C_{1-20}$) alkyl-capped or uncapped polyoxy($C_2$-$C_3$)alkylene of 2 to 200 units;
a represents an integer from 10 to 560;
b represents an integer from 1 to 40, wherein the absolute ratio of a to b is about 2.5 to about 35 and wherein the average integer sum of a+b is in the range of 11 to 600; and
c represents an integer from 0 to 10, wherein the absolute ratio of b to c is no less than about 4;
ii) about 18 to about 50 wt % of the emulsion comprises an oil phase selected from silicone oil, hydrocarbon oil, and mixtures thereof; and
iii) about 50 to about 90 wt % of the emulsion comprises a water phase having a solution pH of about 2 to about 12, with about 0.1 to about 40 wt % added electrolyte, comprising aluminium zirconium salts.

* * * * *